United States Patent [19]

Vida

[11] 4,029,662

[45] June 14, 1977

[54] METHOD OF MAKING BARBITURIC ACID DERIVATIVES

[75] Inventor: Julius A. Vida, Greenwich, Conn.

[73] Assignee: Bristol-Myers Company, New York, N.Y.

[22] Filed: Apr. 30, 1976

[21] Appl. No.: 682,178

[52] U.S. Cl. ............................................. 260/257
[51] Int. Cl.$^2$ .................................... C07D 239/62
[58] Field of Search .................................. 260/257

[56] References Cited

UNITED STATES PATENTS

| 3,635,980 | 1/1972 | Vida et al. | 260/257 |
| 3,784,547 | 1/1974 | Samour | 260/257 |
| 3,947,443 | 3/1976 | Vida | 260/257 |

OTHER PUBLICATIONS

Yardley et al., "Introduction of the Methoxymethyl Ether Protecting Group," Synthesis, Apr. 1976, pp. 244.

*Primary Examiner*—Paul M. Coughlan, Jr.
*Attorney, Agent, or Firm*—Irving Holtzman; Morton S. Simon; David J. Mugford

[57] ABSTRACT

There is disclosed an improved process for the preparation of 1,3-bis(alkoxyalkyl)- and 1,3-bis(benzyloxyalkyl)-5,5-disubstituted barbituric acid derivatives, such as 1,3-bis(methoxymethyl)phenobarbital, by reacting e.g., phenobarbital, preferably, a multiple molar excess of dimethoxymethane and an at least equimolar amount of anhydrous stannic chloride based on the amount of phenobarbital.

7 Claims, No Drawings

METHOD OF MAKING BARBITURIC ACID DERIVATIVES

This invention relates to a method of making 1,3-bis-(alkoxyalkyl)- and 1,3-bis(benzyloxyalkyl)-5,5-disubstituted barbituric acid compounds. More specifically, this invention relates to an improved method for the preparation of 1,3-bis-(alkoxyalkyl)-5-ethyl-5-phenyl barbituric acid, e.g., 1,3-bis-(methoxymethyl)-phenobarbital.

Various techniques for the preparation of 1,3-bis-(methoxymethyl)phenobarbital are known in the art. One method involves reacting the mono-sodium salt of phenobarbital in a polar solvent with a halomethyl methyl ether. However, even when an excess of the ether is employed, no more than half of the phenobarbital salt is converted into the desired product, the remaining half being converted into free phenobarbital.

U.S. Pat. No. 3,920,656, issued Nov. 18, 1975, describes a method for obtaining much higher yields of 1,3-bis(alkoxyalkyl)- or 1,3-bis(benzyloxyalkyl)-5,5-disubstituted barbituric acid compounds by reacting a 5,5-disubstituted barbituric acid, e.g., phenobarbital, with two molar proportions of certain alkaline materials to form a di-salt in the reaction mixture and then reacting the product with two molar proportions of a haloalkyl alkyl ether or a haloalkyl benzyl ether. Examples of the alkaline materials which may be used include sodium hydride, potassium hydride, lithium hydride, potassium tertiary butoxide, lithium hydroxide or mixtures thereof. The reaction is conducted in an inert solvent for the phenobarbital. This method as applied to the preparation of 1,3-bis(methoxymethyl)-phenobarbital is illustrated by the following equation:

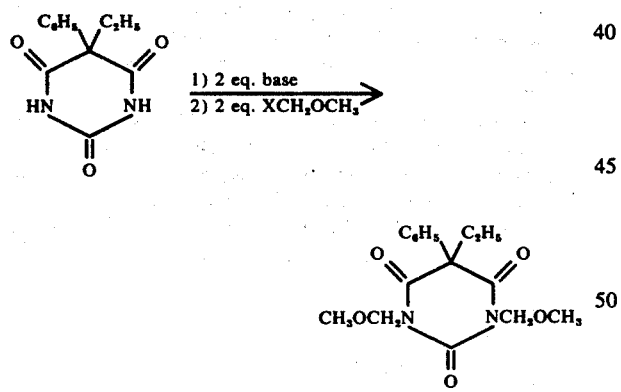

Another two step process for the preparation of 1,3-bis(methoxymethyl)phenobarbital, evaluated by applicant, is illustrated by the following reactions:

1st. STEP

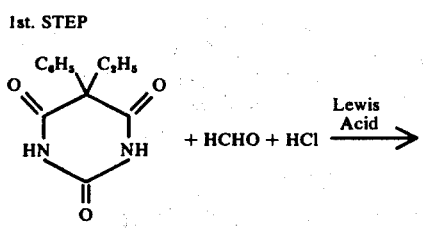

-continued

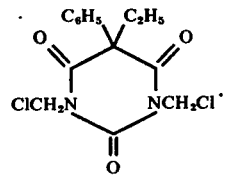

2nd STEP

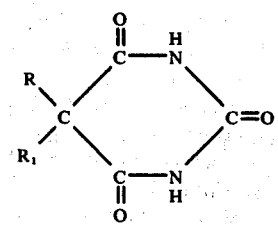

Step 1 of this process is the subject of U.S. Pat. No. 3,947,443, issued Mar. 30, 1976.

It is an object of this invention to provide an improved process for the preparation of a 1,3-bis(alkoxyalkyl)- or a 1,3-bis(benzyloxyalkyl)-5,5-disubstituted barbituric acid derivative.

It is a more specific object of this invention to provide an improved process for the preparation of 1,3-bis(methoxymethyl)phenobarbital in high yields, which process does not involve the use of substantial quantities of chloromethyl methyl ether, thereby avoiding the use of elaborate safety measures to comply with OSHA standards, and which process does not employ a mixture of formaldehyde and hydrochloric acid, which combination is known to be carcinogenic.

These and other objects are achieved by the practice of this invention which, briefly, comprises reacting in one step a 5,5-disubstituted barbituric acid having the formula:

$$\begin{array}{c} R \\ R_1 \end{array} \! \! \! \! \! \! \! \! \! \! \! \! \! \! \! \! \! \! \begin{array}{c} O \\ \| \\ C-N \\ \\ C \\ \\ C-N \\ \| \\ O \end{array} \! \! \! \! \! \! \! \! \! \! \! \! \! \! \! \! \! \! \begin{array}{c} H \\ \\ \\ C=O \\ \\ \\ H \end{array}$$

wherein R and $R_1$ are phenyl and ethyl respectively, or R and $R_1$ are individually or both alkyl or alkenyl having 2 to 5 carbon atoms or cycloalkenyl having 5 to 7 carbon atoms, with at least 2 moles of a dialkoxymethane or a dibenzyloxymethane and an at least equimolar amount of anhydrous stannic chloride based on the amount of phenobarbital to obtain a product having the formula:

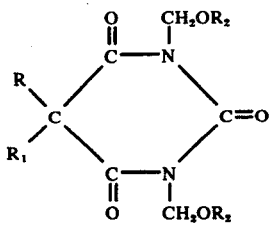

wherein R and $R_1$ are the same as previously described and each $R_2$ is the same and is an alkyl group having from 1 to 4 carbon atoms or benzyl. The reaction is preferably carried out in a reaction inert solvent. Suitable solvents include, for example, benzene; toluene; chlorinated solvents, e.g., tetrachloromethane, dichloromethane, chloroform and hexachloroethane; acetonitrile; and the like.

Preferably, a sufficient amount of the appropriate dialkoxymethane or dibenzyloxymethane is employed to facilitate the reaction and act as a solvent therefor.

Preferably, the reactants are phenobarbital, dimethoxymethane and anhydrous stannic chloride. The preferred embodiment is illustrated by the following equation:

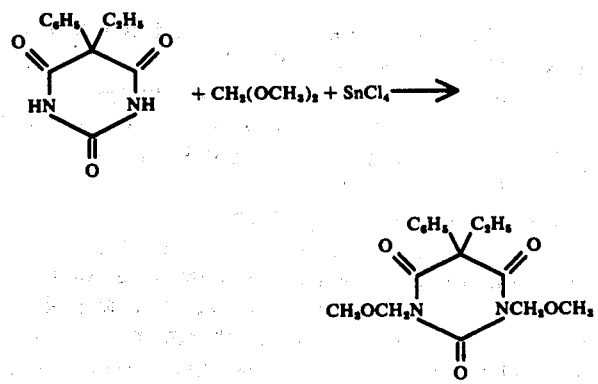

In this reaction, the dimethoxymethane acts as both a reagent and a solvent for the reaction. Preferably, at least 10 moles of dimethoxymethane per mole of phenobarbital are used. The reaction is preferably conducted at about the boiling point of dimethoxymethane at atmospheric pressure. The reaction is allowed to proceed to completion as determined by thin layer chromotography and generally takes about 24 hours.

The process of this invention has several advantages over heretofore known processes for preparing 1,3-bis-(alkoxyalkyl)- or 1,3-bis(benzyloxyalkyl)-5,5-disubstituted barbituric acid compounds and more specifically 1,3-bis(methoxymethyl)phenobarbital. The reaction is a one step process and is therefore more economical than heretofore known multiple step processes. Moreover, the process does not employ chloromethyl methyl ether. Although some chloromethyl methyl ether is generated in situ during the course of the reaction, at any one time the amount of this compound may be sufficiently low as to preclude the requirement for elaborate safety measures other than the use of a slight vacuum and scrubber system which would be acceptable to OSHA. Moreover, the procedure does not employ a mixture of formaldehyde and hydrochloric acid which is known to be carcinogenic.

The products obtained by the practice of this invention are useful as anticonvulsive agents for treating convulsions and seizures in warm-blooded animals while exhibiting substantially no hypnotic activity.

The following examples illustrate the best modes contemplated for carrying out this invention:

EXAMPLE 1

There were dissolved in 100 ml. of dimethoxymethane (85.93 g.; 1.13 mole) 23.2 g. of phenobarbital (0.1 mole). To this solution were added over a period of 20 minutes 30 ml. of anhydrous stannic chloride (66.8 g.; 0.26 mole). The resultant solution was stirred for 24 hours at reflux temperature. The reaction was conducted under an atmosphere of nitrogen using a condenser connected to a dry ice-acetone trap protected by a drying tube to trap out any condensate suitable for analysis. The purpose of trapping out was to establish the presence or absence at any time of any chloromethyl methyl ether that may have been formed in the course of the reaction. After 24 hours, the reaction mixture was poured into 500 g. of a mixture of ice and water and stirred for another 2 hours. A white solid precipitate appeared which was removed by filtration and then washed twice with 50 ml. of water. The crude product was dried to give 29.2 g. of product which represented 91% of the theoretical possible amount of product based on the amount of phenobarbital employed. This product was determined to be pure 1,3-bis-(methoxymethyl)phenobarbital by comparison on thin layer chromatogram with a known sample of 1,3-bis(methoxymethyl)phenobarbital. The crude product was dissolved in 300 ml. of 80% hot isopropanol, treated with charcoal, filtered and crystallized to give a total of 26 g. of product having a melting point of 117°–119° C. This represented a yield of 81% of the theoretical possible amount based on the amount of phenobarbital. A second recrystallization from 300 ml. of 80% isopropanol gave 22.6 g. of product having a melting point of 118°–119° C. which represented a 70% theoretical yield based upon the amount of phenobarbital. Small amounts of products of undetermined composition were also obtained during the course of this reaction.

Following the procedure of the preceding example, in separate experiments, the stannic chloride was replaced by a catalytic amount of stannic chloride (rather than a 2.6:1 molar amount of stannic chloride based on the amount of phenobarbital) and by an approximate equivalent molar amount of the following compounds:

Trifluoroacetic acid
Conc. $H_2SO_4$
Polyphosphoric acid
Boron trifluoride etherate
Stannic bromide
Aluminum chloride
Hydrofluoro boric acid
Sodium hexafluoroantimonate
Ammonium tetrafluoroantimonate
Boron trifluoride-urea complex None of these experiments were successful in obtaining 1,3-bis-(methoxymethyl)phenobarbital. Thus, these experiments demonstrate that the reaction is specific to anhydrous stannic chloride and that the anhydrous stannic chloride does not act merely as a catalyst.

EXAMPLE 2

There were suspended in 200 ml. of dibenzyloxymethane (210.94 g., 0.92 mole) 23.2 g. of phenobarbital (0.1 mole). To this suspension were added over a period of 20 minutes 33 ml. of anhydrous stannic chloride (73.5 g., 0.28 mole). The reaction mixture was stirred for 24 hours at 100°–150° C. After 24 hours, the reaction mixture was poured into 500 g. of a mixture of ice and water and stirred for another 2 hours. A white solid precipitate appeared which was removed by filtration and then washed twice with 50 ml. of water. The crude product was dried to give 50.2 g. of product which represented a yield of 87% of theoretical, based on the amount of phenobarbital employed. This product was determined to be pure 1,3-bis(benzyloxymethyl)-phenobarbital by comparison on thin layer chromatogram with a known sample of 1,3-bis(benzyloxymethyl)phenobarbital. Recrystallization of the product from 300 ml. of 80% ethanol gave a total of 45 g. having a melting point of 74°–75° C. This represented a yield of 78% of theoretical, based on the amount of phenobarbital. A second recrystallization from 300 ml. of 80% ethanol gave 40.1 g. of product having a melting pont of 74.5°–75.5° C. which represented a yield of 70% of theoretical, based upon the amount of phenobarbital. Small amounts of products of undetermined composition were also obtained during the course of this reaction.

EXAMPLE 3

There were suspended in 191 ml. of di-(n)-butoxymethane (160 g., 1.0 mole) 23.2 g. of phenobarbital (0.1 mole). To this suspension were added over a period of 30 minutes 36 ml. of anhydrous stannic chloride (81.3 g., 0.31 mole). The reaction mixture was stirred for 24 hours at 95°–100° C. After 24 hours, the reaction mixture was poured into 500 g. of a mixture of ice and water and stirred for another 2 hours. A white solid precipitate appeared which was removed by filtration and then washed twice with 50 ml. of water. The crude product was dried to give 29.8 g. of product which represented a yield of 73.6% of theoretical, based on the amount of phenobarbital employed. This product was determined to be pure 1,3-bis(n-butoxymethyl)-phenobarbital by comparison on thin layer chromatogram with a known sample of 1,3-bis(n-butoxymethyl)-phenobarbital. Recrystallization of the product from 300 ml. of 80% isopropanol and treatment with charcoal gave a total of 26 g. of product having a melting point of 70°–72° C. This represented a yield of 64% of theoretical, based on the amount of phenobarbital. A second recrystallization from 300 ml. of 80% isopropanol gave 23.5 g. of product having a melting point of 71°–72° C. which represented a yield of 58% of theoretical, based upon the amount of phenobarbital. Small amounts of products of undetermined composition were also obtained during the course of this reaction.

EXAMPLE 4

There were suspended in 100 ml. of dimethoxymethane (85.93 g., 1.13 mole) 18.7 g. of barbital (0.1 mole). To this suspension were added over a period of 15 minutes 28 ml. of anhydrous stannic chloride (62.32 g., 0.24 mole). The resultant solution was stirred for 24 hours at 42°–45° C. After 24 hours the raction mixture was poured into 400 g. of a mixture of ice and water and stirred for another 2 hours. The product was extracted into ethyl acetate, the solvent evaporated and the crude product was purified by column chromatography on silica gel. Elution with a benzene-ethyl acetate mixture (8:2 by volume) provided pure 1,3-bis(methoxymethyl)-5,5'-diethyl-barbituric acid (15 g., an oil). This represents a yield of 55% of theoretical, based on the amount of barbital employed. This product was determined to be pure 1,3-bis(methoxymethyl)-5,5'-diethylbarbituric acid by comparison on thin layer chromatogram with a known sample of 1,3-bis(methoxymethyl)-5,5'-diethylbarbituric acid. Microanalysis of this compound was within ± 0.3% of the theoretical values for carbon, hydrogen and nitrogen. Infrared spectrum was obtained for the compound as expected. Products of undetermined composition were also obtained during the course of this reaction.

EXAMPLE 5

The procedure of Example 4 was repeated except that 23.8 g. of 5-allyl-5'-(2-pentyl)-barbituric acid were utilized in place of the 18.7 g. barbital. There were obtained 17 g. of 1.3-bis(methoxymethyl)-5-allyl-5'-(2-pentyl)-barbituric acid as an oil. This represents a yield of 52% of theoretical, based on the amount of 5-allyl-5'-(2-pentyl)-barbituric acid. The product was characterized as described under Example 4.

EXAMPLE 6

The procedure of Example 4 was repeated except that 23.8 g. of 5-allyl-5'-(2-pentyl)-barbituric acid were utilized in place of the 18.7 g. barbital and 200 ml. of dibenzyloxymethane (210.94 g., 0.92 mole) were utilized in place of the dimethoxymethane. There were obtained 24 g. of 1,3-bis(benzyloxymethyl)-5-allyl-5'-(2-pentyl)-barbituric acid as an oil. This represents a yield of 50% of theoretical, based on the amount of 5-allyl-5'-(2-pentyl)-barbituric acid. The product was characterized as described under Example 4.

EXAMPLE 7

The procedure of Example 4 was repeated except that 23.6 g. of 5-ethyl-5'-(1-cyclohexen-1-yl)-barbituric acid were utilized in place of the 18.7 g. barbital. There were obtained 18 g. of 1,3-bis(methoxymethyl)-5-ethyl-5'-(1-cyclohexen-1-yl)-barbituric acid. This represents a yield of 55% of theoretical based on the amount of 5-ethyl-5'-(1-cyclohexen-1-yl)-barbituric acid. The product was characterized as described under Example 4.

What is claimed is:

1. A process for the preparation of a barbituric acid derivative having the formula:

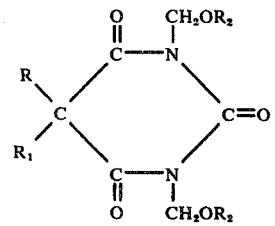

wherein R and $R_1$ are phenyl and ethyl respectively, or R and $R_1$ are individually or both alkyl or alkenyl, having 2 to 5 carbon atoms or cycloalkenyl having 5 to 7 carbon atoms, and each $R_2$ is the same and is an alkyl group having from 1 to 4 carbon atoms or benzyl, which process comprises reacting in one step a 5,5-disubstituted barbituric acid having the formula:

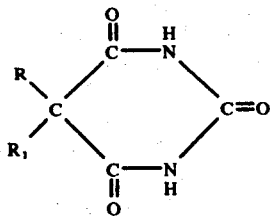

wherein R and R₁ are phenyl and ethyl respectively, or R and R₁ are individually or both alkyl or alkenyl, having 2 to 5 carbon atoms or cycloalkenyl having 5 to 7 carbon atoms, with at least 2 moles of a dialkoxymethane or a dibenzyloxymethane per mole of said barbituric acid and an at least equimolar amount of anhydrous stannic chloride based on the amount of said barbituric acid.

2. The process as defined in claim 1, wherein said reactants are phenobarbital, dimethoxymethane and anhydrous stannic chloride and wherein the product obtained is 1,3-bis(methoxymethyl)phenobarbital.

3. The process as defined in claim 2, wherein said reaction is conducted at about the boiling point of dimethoxy-methane.

4. The process as defined in claim 2, wherein said reaction mixture contains at least 10 moles of dimethoxymethane per mole of phenobarbital.

5. The process as defined in claim 2, wherein said dimethoxymethane and anhydrous stannic chloride are present in an amount of about 11.4 mole and 2.6 mole, respectively, per mole of phenobarbital.

6. The process as defined in claim 1, wherein said dialkoxymethane or said dibenzyloxymethane is employed in an amount sufficient to promote the reaction and serve as a solvent therefor.

7. The process as defined in claim 1, wherein said reaction is carried out in a reaction - inert solvent.

* * * * *